United States Patent [19]
Floch et al.

[11] Patent Number: 5,841,524
[45] Date of Patent: Nov. 24, 1998

[54] COMPACT DEVICE FOR MONITORING THE COATING OF A MOVING FILAMENTARY PRODUCT

[75] Inventors: Bernard Floch, Chaumont En Vexin; Didier Rolland, Sannois, both of France

[73] Assignee: Alcatel Alsthom Compagnie Generale D'Electricite, Paris, France

[21] Appl. No.: 773,359

[22] Filed: Dec. 26, 1996

[30] Foreign Application Priority Data

Dec. 28, 1995 [FR] France .................................. 95 15660

[51] Int. Cl.⁶ .......................... G01N 21/00; G01B 11/14; C03B 37/07; B05D 3/14
[52] U.S. Cl. .......................... 356/73; 356/73.1; 356/237; 356/429; 356/375; 356/385; 356/430; 250/559.34; 427/10; 65/382; 65/485; 65/491; 65/158; 65/160
[58] Field of Search .......................... 356/73.1, 73, 23.7, 356/238, 429, 385, 430, 375; 65/382, 485, 491, 435, 158, 160; 427/9–10; 250/559.34

[56] References Cited

U.S. PATENT DOCUMENTS

| | | |
|---|---|---|
| 3,565,536 | 2/1971 | Wuellner et al. |
| 4,042,723 | 8/1977 | Presby ........................................ 356/73.1 |
| 4,124,728 | 11/1978 | Marcuse et al. .......................... 356/429 |
| 4,390,897 | 6/1983 | Smithgall, Sr. ........................... 356/73.1 |

OTHER PUBLICATIONS

Patent Abstract of JP 55 113 636, Takahashi Shiro, Manufacture of Optical Fiber, Sep. 2, 1980.

*Primary Examiner*—Frank G. Font
*Assistant Examiner*—Jason D. Vierra-Eisenberg
*Attorney, Agent, or Firm*—Sughrue, Mion, Zinn, Macpeak & Seas, PLLC

[57] ABSTRACT

An apparatus for monitoring a moving filamentary product having a device for monitoring the centering of the filamentary product relative to the coating, and a device for monitoring the quality of the coating. The centering monitoring device includes two light sources positioned at 90° to each other in a plane perpendicular to the filamentary product. The coating quality monitoring device includes an optical receiver disposed between the two light sources in the same plane, and at 45° to each of them, to receive the light beams reflected by the coating.

11 Claims, 2 Drawing Sheets

COMPACT DEVICE FOR MONITORING THE COATING OF A MOVING FILAMENTARY PRODUCT

BACKGROUND OF THE INVENTION

The field of the invention is that of the fabrication of filamentary products. To be more precise, the invention concerns monitoring the coating of such filamentary products. This monitoring covers two aspects, namely the centering of the product relative to the coating means, on the one hand, and the quality of the coating (i.e. the detection of defects), on the other hand.

One particular field of application of the invention is that of coating optical fibers. This aspect is described in more detail below. However, the invention is not limited to optical fibers, but applies equally to the production of any moving filamentary product, whether sheathed or not.

The operations of monitoring the centering and the quality of the coating are conventional and necessary in all optical fiber fabrication methods. The functions of the coating include protecting the fiber from environmental attack. It is generally a plastics material coating based on a resin that can be polymerized. The coating often comprises two layers that can be polymerized by ultraviolet light, of the epoxy-acrylate or urethane-acrylate type.

A coating of this kind must obviously be perfectly distributed and perfectly regular if the transmission of optical signals is not to be disturbed. Otherwise, microcurvature phenomena can occur, causing losses.

Prior art machines for fabricating optical fibers therefore include two monitoring instruments:

- a device for monitoring the centering of the fiber which visualizes the position of the fiber within the coating to enable dynamic adjustment of the position of the coating devices;
- a device for monitoring the quality of the coating enabling the onset of coating surface defects to be detected during production.

Document DE-A-1 573 795 discloses a device using light transmitted by the optical fiber to monitor the centering of the fiber and to detect impurities within the coating. Another device is disclosed in document DE-A-2 855 598; once again, transmitted light is used to monitor the centering of the fiber. It is also used, in a manner that is not explained, to monitor the quality of the coating.

The major problem with these devices is that of their overall size. The height of the fiber-drawing machines is restricted and it is often very difficult to install these devices, and in particular the ergonomic features offered to users are minimal.

What is more, the prior art centering systems usually employ gas lasers (for example He Ne lasers). These lasers are very bulky or have a limited service life incompatible with the 24 hours a day operation of the fiber drawing machines. It is well known that the smaller the gas laser tube, the shorter its service life.

SUMMARY OF THE INVENTION

An objective of the invention is to overcome these disadvantages of the prior art.

To be more precise, one objective of the invention is to provide means for monitoring the quality of the coating of a filamentary product, such as an optical fiber, which are less bulky than prior art devices.

Another objective of the invention is to provide such monitoring means which are less costly than prior art devices and easier to use.

A further objective of the invention is to provide such monitoring means enabling on-line measurements and monitoring, in order to improve the quality of the products fabricated. In particular, the monitoring means of the invention must enable the detection of any repetitive defect and any behavior defect (product or machine).

A supplementary objective of the invention is to provide such monitoring means enabling losses to be limited in situations where a defect is found.

The above objectives, and others that will emerge below, are achieved in accordance with the invention by a device for monitoring the coating of a moving filamentary product, comprising at least one light source cooperating with means for monitoring the centering of said filamentary product relative to coating means and with means for monitoring the quality of said coating, in which device said means for monitoring the quality of said coating comprise an optical receiver disposed to receive the light beams reflected by said coating.

Accordingly, in accordance with the invention, the light source is used in two different ways, for two independent functions. As will emerge below, light passing through the product can be used for centering while reflected light from the same source is used to assess the quality of the coating.

The new structure evidently minimizes the overall size of the equipment needed to monitor two essential control parameters. This overcomes the problem of the lack of room in fiber drawing machines, especially vis-à-vis the devices described in documents DE-A-1 573 795 and DE-A-2 855 598 which require emitter and receiver means on opposite sides of the fiber.

Furthermore, it is evident that the use of the same light source for two separate functions reduces the cost of the monitoring means.

The device of the invention advantageously comprises two light sources at 90° to each other in a plane perpendicular to the filamentary product, the light beams emitted by the light sources crossing at the center of said filamentary product if the latter is correctly centered.

In this case the centering monitoring means preferably comprise two frosted screens each disposed perpendicularly to the light beam from one of the light sources, the filamentary product traveling between each light source and the corresponding frosted screen.

Accordingly, the operator sees on the screens diffraction fringes created by the light beams passing through the product (through the cladding and the silica in the case of an optical fiber). If the product is correctly centered, the light spot corresponding to its optical center is at equal distances from two spots corresponding to the transitions between the product and its coating.

The optical receiver is advantageously disposed between the light sources, in the same plane and at 45° to each of them.

This receiver therefore receives the light spot from the light sources reflected from the surface of the fiber. Analysis of this reflection enables detection of any coating defects.

In one embodiment of the invention the receiver comprises pick-up optics, a photodetector and an amplifier system.

The light sources are advantageously semiconductor lasers. This choice is particularly advantageous, compared to the prior art equipment using gas lasers, especially with regard to the resulting overall size and service life.

The invention can be used to monitor the coating of very many filamentary products and in particular optical fibers and enameled copper wires.

In an advantageous embodiment of the invention the device comprises means for adjusting an alarm threshold representative of a level of deterioration of the quality of the coating of the filamentary product.

In accordance with another preferred feature, it may comprise means for filtering the signal delivered by the receiver, the cut-off frequency of which is adjustable in order to detect particular repetitive defects.

The pass-band of the filter means is advantageously adjusted automatically in accordance with the linear speed of said linear product.

Finally, the device of the invention can cooperate with external processor means continuously analyzing the analog signal supplied by the receiver. For example, a real time fast Fourier transform (FFT) analyzer can identify the source of vibration of the fiber or the pitch of periodic defects.

Additionally, continuous recording of the fiber drawing parameters enables qualitative production monitoring.

BRIEF DESCRIPTION OF THE DRAWINGS

Other features and advantages of the invention will emerge from a reading of the following description of one preferred embodiment of the invention given by way of non-limiting and illustrative example only and from the accompanying drawings in which.

DESCRIPTION OF THE PREFERRED EMBODIMENT

Figure 1:
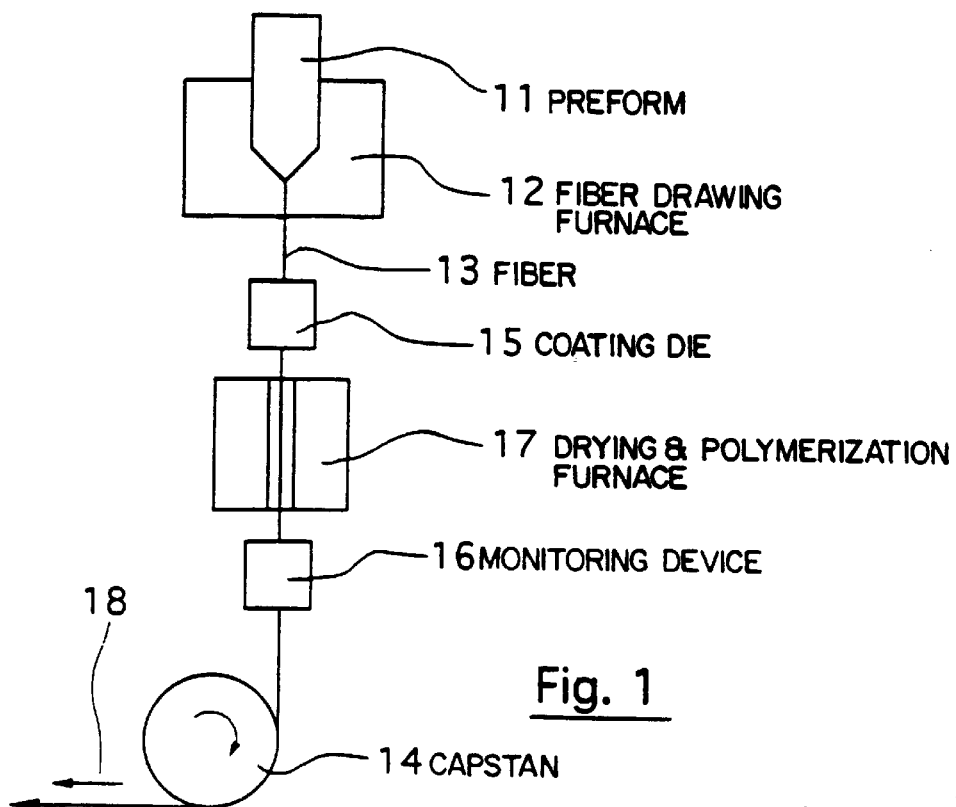
FIG. 1 is a schematic representation of a fiber drawing machine of a type that is known in itself, equipped with the device of the invention.

The embodiment described below is more particularly concerned with the fabrication of optical fibers. The principles of fabrication of these fibers are briefly summarized with reference to FIG. 1.

An optical fiber is made in two phases: first a preform, or condensed form of the fiber, is produced in the form of a cylinder having a diameter of between 14 and 70 mm, for example and a length of 60 to 100 cm. A preform of this kind can be used to fabricate 6 to 300 km of fiber.

The fiber drawing operation proper is that of drawing the preform. The preform 11 is introduced into a fiber drawing furnace 12, the temperature in which is generally in the order of 2,000° C., depending on the nature and the quantity of the dopants. The preform becomes viscous, so that it "runs" under its own weight. A fiber 13 is obtained in this way (generally with a diameter of 125 μm).

The rate of descent of the preform 11 is in the order of a few centimeters per minute. The fiber 13 is entrained by a capstan 14 at a speed from a few tens to at least a few hundreds of meters per minute.

To protect the fiber from attack by the environment it is necessary to cover it with a plastics coating, generally in the form of a resin that can be polymerized. The resin is applied to the fiber 13 in liquid form, after the latter leaves the fiber drawing furnace 12, using a coating die 15. The coating is generally made up of two layers that can be polymerized easily, based on epoxy-acrylate or urethane-acrylate, for example. The inside layer is softer, to limit microcurvature losses.

The fiber is then passed into a drying and polymerization furnace 17 which activates polymerization by thermal energy and/or ultraviolet radiation in order to solidify the coating before the fiber reaches the capstan 14.

Finally, the fiber is fed off (18) to be stored on a drum.

The function of the device 16 of the invention is to verify the quality of the coating and to facilitate centering of the fiber in the coating device 15. It is disposed downstream of the exit from the furnace 17.

The device 16 comprises optical means and electronic means.

Figure 2:
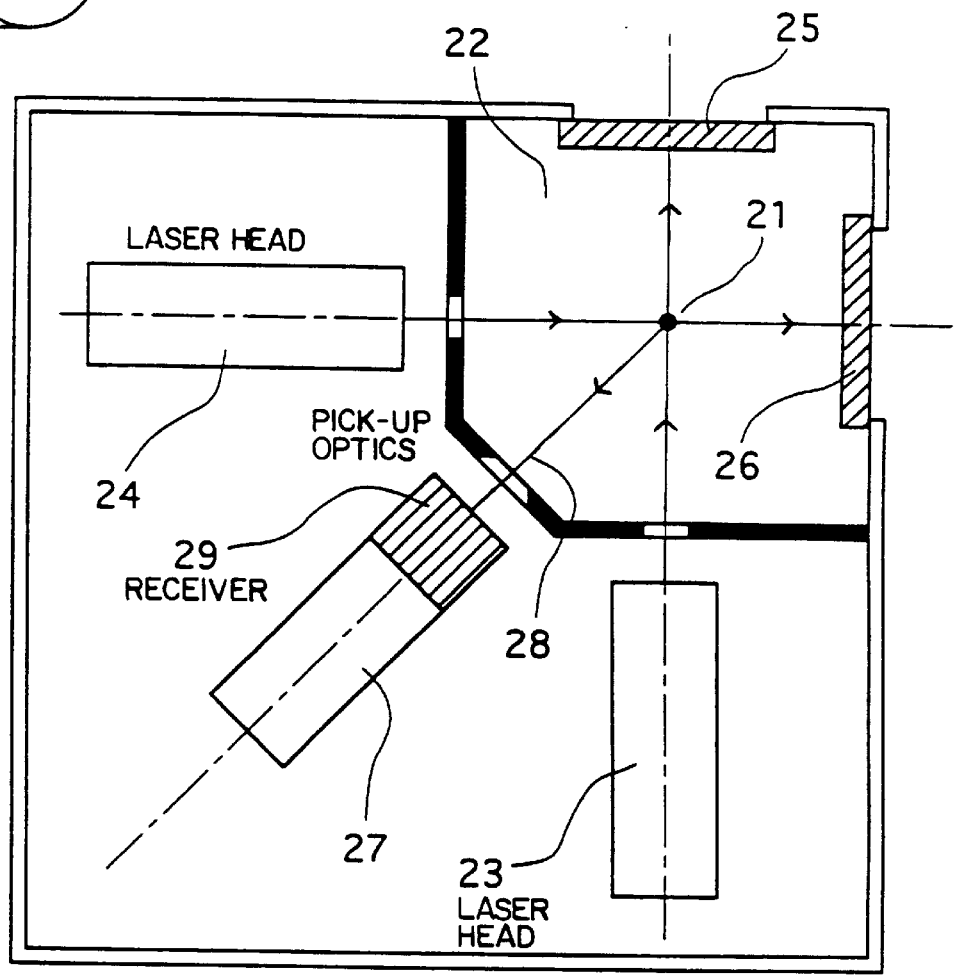
FIG. 2 shows the layout of the optical components in the device of the invention.

FIG. 2 shows the layout of the optical components.

The fiber 21 passes through a fiber passage 22. Two small solid-state laser heads 23, 24 (semiconductor lasers) emit a light beam in the visible domain (red light, for example) towards the fiber. The two laser heads are the same horizontal plane, i.e. the same plane perpendicular to the fiber 21. The light beams are at 90° to each other and illuminate the fiber 21 at a single point.

Two frosted screens 25, 26 are disposed perpendicularly to the axis of the lasers 23, 24 so that the fiber 21 passes between the laser head 23, 24 and the corresponding frosted screen 25, 26.

The operator therefore sees on the screens 25, 26 diffraction fringes created by the passage of the laser beam through the cladding and the silica. The operator sees a horizontal line in which the epoxy/epoxy and epoxy/silica transition areas are shown by a local increase in brightness. The fiber behaves as a cylindrical lens and produces a light spot by concentrating the light rays. The position of this light spot indicates the optical center.

If the fiber is at the center of the cladding, the spots corresponding to the epoxy layers are at equal distances from the optical center, on opposite sides. If not, the operator can dynamically modify the relative position of the fiber and the coating device in order to bring about the required centering.

This operation can also be automated. For example, the frosted screens may be replaced by sensors delivering a current image to a processor unit where it is compared with a reference image in order to control the centering means.

The device of the invention further comprises means for detecting coating defects, comprising pick-up optics 29 (shown in detail in FIG. 3) and a receiver 27. These means are in the same plane as the laser heads 23, 24 and at 45° to each of the latter.

The pick-up optics 29 receive the reflection 28 from the surface of the fiber 21 of the light spot produced by the two laser beams. Analysis of the reflected light identifies various defects that may appear in the fiber coating. As will emerge below, by adjusting the electronics it is possible to specify the type of defects looked for.

Figure 3:
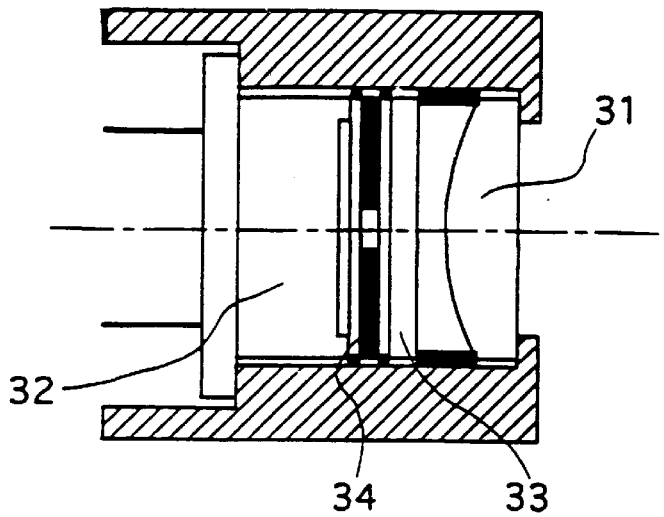
FIG. 3 shows in detail the pick-up optics of the receiver from FIG. 2.

FIG. 3 shows the pick-up optics 29 from FIG. 2. They comprise a lens 31 the focal length of which matches the distance between the fiber and the detector (photodiode) 32, a red filter 33 and a filter hole 34.

Figure 4:
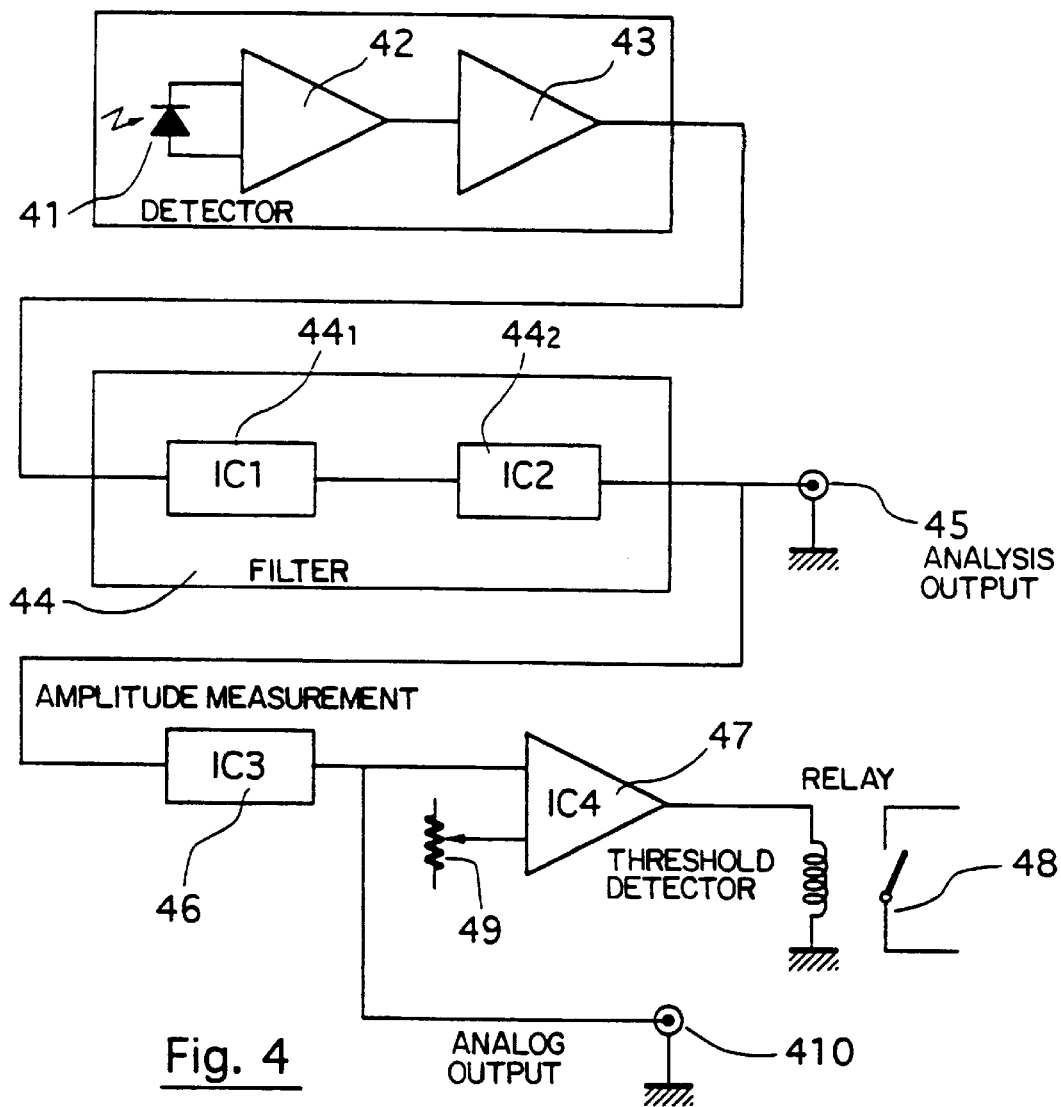
FIG. 4 is a simplified block diagram of the electronic components of the device of the invention.

The detector 32 is connected to the electronic processor means shown in FIG. 4. The essential role of the latter means is to detect defects and to trip an alarm or take any other action in response to deterioration in the quality of the fiber coating during production.

The photodiode 41 is associated with a preamplifier 42, the output signal from which is amplified by an output amplifier 43. These components constitute the electronics of the measurement head. They are connected to the processor electronics, for example by a coaxial cable.

The processor electronics comprise a selector filter 44 made up of two circuits 44₁ and 44₂ constituting a band-pass filter. The output 45 of the filter (called the analysis output) is available for specific processing and/or recording. It also feeds an amplitude measuring circuit 46 feeding a threshold detector 47.

The filter 44 selects the type of defect looked for. In the case of a repetitive defect, for example, the cut-off frequency is adjusted to suit the pitch of the observed defect.

The filter also assures that the system is not influenced by the background illumination (50/100 Hz generated by fluorescent lighting).

Finally, provision may be made for automatic adjustment of the pass-band of the filter in accordance with the linear speed of the fiber.

If the amplitude of the signal exceeds a given value, the threshold detector 47 causes a relay 48 to be energized, which trips the alarm. More generally, the contacts of the relay 48 are available for any external use, such as sending audible and/or luminous alarm indications, inkjet marking the fiber, etc. In the event of an alarm, the operator can stop the machine, remedy the problem and then restart fiber drawing, so saving the remainder of the preform.

The alarm threshold may be adjusted as required by means of the potentiometer 49.

The output 410 (analog output) is also available for processing and/or recording. The analog output 410 is accordingly used for continuous recording of the mean value of the "roughness" of the coating. This assures qualitative monitoring of production.

The analysis output 45 can be used to visualize the nature of the disturbance on an oscilloscope or a spectrum analyzer. Using a real time FFT analyzer, for example, it also can identify the source of vibration of the fiber or, in the case of repetitive defects, the pitch of the latter.

The device of the invention therefore enables detection of any repetitive defect for which the pitch is within the pass-band of the filter 44 (which can be adjusted if necessary to look for a particular defect), together with any behavior defect (product or machine), by analysis of the frequency of the signal available at the analysis output 45.

The measurement head is very simple to use. The system is positioned so that the fiber passes through the center of the measuring conduit (22, FIG. 2). The frosted screens makes it a simple matter to center the measurement head around the fiber to be analyzed visually.

It will be remembered that the device of the invention is not usable only on optical fibers. It can also be used on any moving filamentary product, whether sheathed or not, such as enameled copper wires. It can also be used for detecting surface defects on flat products (in which case it is used without the centering part).

What is claimed is:

1. A device for monitoring a coating applied by a coating means onto a moving filamentary product, comprising:
    two light sources for emitting light beams which cross at the center of said filamentary product;
    means for monitoring the centering of said filamentary product relative to said coating means, said means for monitoring the centering of said filamentary product receiving said emitted light beams from said two light sources after said emitted light beams have interacted with said filamentary product; and
    an optical receiver for monitoring the quality of said coating, said optical receiver disposed to receive said light beams emitted from said two light sources and reflected by said coating.

2. A device according to claim 1, wherein said two light sources are positioned at 90° to each other in a plane perpendicular to said filamentary product, light beams emitted by said two light sources crossing at the center of said filamentary product.

3. A device according to claim 1, wherein said means for monitoring the centering of said filamentary product comprises two frosted screens, each disposed perpendicularly to the light beam from one of said two light sources, said filamentary product traveling between each light source and the corresponding frosted screen.

4. A device according to claim 1, wherein said optical receiver is disposed between said two light sources, in the same plane and at 45° to each of them.

5. A device according to claim 1, wherein said optical receiver comprises pick-up optics, a photodetector and an amplifier system.

6. A device according to claim 1, wherein said two light sources are semi-conductor lasers.

7. A device according to claim 1, wherein said filamentary product is selected from the group consisting of optical fibers and enameled copper wires.

8. A device according to claim 1, further comprising:
    an alarm threshold representative of a level of deterioration of the quality of said coating of said filamentary product; and
    a means for adjusting said alarm threshold.

9. A device according to claim 1, further comprising a means for filtering a signal delivered by said optical receiver, said means for filtering having an adjustable cut-off frequency.

10. A device according to claim 9, wherein said means for filtering has a pass-band which is adjusted automatically in accordance with a linear speed of said filamentary product.

11. A device according to claim 1, further comprising an external processor means that continuously analyzes an analog signal produced by said optical receiver.

* * * * *